United States Patent [19]

Cheung

[11] 4,376,673

[45] Mar. 15, 1983

[54] METHOD FOR ETCHING DENTAL PORCELAIN

[75] Inventor: Peter P. L. Cheung, Gulph Mills, Pa.

[73] Assignee: Pennwalt Corporation, Philadelphia, Pa.

[21] Appl. No.: 235,809

[22] Filed: Feb. 19, 1981

[51] Int. Cl.³ .......................... B44C 1/22; A61C 13/00
[52] U.S. Cl. ..................................... 156/662; 252/79.2; 252/79.3; 252/136; 252/142; 156/663; 156/94; 156/293; 433/228; 433/229; 433/216; 433/218
[58] Field of Search ..................... 252/79.3, 79.4, 136, 252/142, 79.2, 79.1; 156/635, 625, 663, 94, 293, 662; 134/3; 433/9, 202, 206, 208, 217, 218, 228, 229, 180, 181, 191, 216

[56] References Cited

U.S. PATENT DOCUMENTS 3,847,688 11/1974 Gillice ................................ 252/79.3
3,899,437 8/1975 Regan et al. ....................... 252/136
4,117,595 10/1978 Ibsen et al. ........................... 433/218

Primary Examiner—Edward C. Kimlin
Assistant Examiner—F. K. Wine
Attorney, Agent, or Firm—John S. Munday

[57] ABSTRACT

The method of etching a porcelain dental appliance insitu including the steps of contacting the porcelain with a buffered solution containing trace amounts of hydrogen fluoride and removing the solution after sufficient time has elapsed to etch the porcelain. Preferred solutions are buffered at a pH from about 2.0 to about 6.0 and most preferably from about 3.5 to about 4.5. Contact time of the solution with porcelain ranges from about five minutes to from about five to about thirty minutes or longer.

The solution preferably contains an alkali metal fluoride dissolved in a weak acid. In a preferred embodiment, the solution contains about one to about three parts by weight of sodium fluoride dissolved in about 50 parts to about 150 parts by weight of dilute weak acid. The weak acid has a molarity of from about 0.05 molar to about 0.5 molar. The weak acid solution is buffered, if necessary, and has a pH of from about 2.0 to about 6.0 and preferably from about 3.5 to about 4.5 A gelling agent may be added to gel the solution to permit more effective contact of the solution against with the porcelain being treated.

11 Claims, No Drawings

METHOD FOR ETCHING DENTAL PORCELAIN

BACKGROUND OF THE INVENTION

Dental porcelain is a relatively strong ceramic material which is insoluable in oral fluids and has excellent aesthetic qualities. It is formed from a fine ceramic powder which has been pigmented to produce the color and translucency of human teeth, and which has been formed into a paste and fused to form the ceramic body. Because porcelain has excellent tissue compatibility and a relatively long lasting life, porcelain and porcelain processing techniques have been used for artificial teeth, inlays, crowns, bridges, and complete dentures.

Porcelain has been limited in its effectiveness in restorative procedures primarily by the major undesirable characteristics of the material, namely brittleness. Due to the brittle nature of porcelain, patients who have permanent attachment of porcelain dental appliances in the mouth often suffer the agony of having fractured porcelain. While the fracture oftentimes does not cause direct pain, a great deal of time, money and dental effort is expended to repair broken porcelain appliances. For example, when a porcelain jacket crown becomes fractured, usually the entire appliance has to be removed and a new appliance made, which is then reattached with a cement.

Some efforts have been made recently to employ polymeric composite materials to restore the defective part of a broken porcelain appliance without removing the appliance from the patient's mouth. This newly attempted technique involves the use of mechanical abrasion to roughen up the surface of the porcelain, followed by application of a silane adhesion promoter with a final step of applying a polymeric composite restorative material with an adhesive. While this method substantially reduces chair time and cost, the composite material many times is not adequately bonded to the porcelain and falls off due to stress and insufficient adhesion. Mechanical roughening improves adhesion, but is ineffective in introducing the microcrevices necessary for positive mechanical locking by the composite materials. Furthermore, there is always the risk of further chipping the porcelain during the roughening-up process, which is usually done by a dental bur.

SUMMARY OF THE INVENTION

An improved method has been discovered for etching porcelain dental appliances to provide the microcrevices necessary to allow positive mechanical locking by composite materials bonded thereto. The method is suitable for use on dental appliances which have already been installed in the patients's mouth and consists of contacting the porcelain with a buffered solution containing trace amounts of hydrogen fluoride, and removing the solution after sufficient time has elapsed to allow the porcelain to be etched. It is preferred that the solution be buffered at a pH of from about 2 to about 6, and most preferably from about 3.5 to about 4.5. The solution may be maintained in contact with the porcelain for sufficient time to cause the porcelain to be etched, so that the effective adhesive bond can be made. This time may range from as little as two or three minutes to a preferred minimum of five minutes. Most preferred is approximately from about five minutes to about thirty minutes for contact time by the solution of the porcelain.

The preferred solution contains a quantity of alkali metal fluoride dissolved in dilute weak acid in an amount sufficient to give a trace amount of hydrogen fluoride. Preferably the solution will contain from about one to about three parts by weight of alkali metal fluoride, preferably sodium fluoride, dissolved in about 50 to about 150 parts by weight of dilute weak acid. The weak acid is diluted to a molarity ranging from about 0.05 molar to about 0.5 molar. If desired, the dilute acid solution may be buffered to a pH ranging from about 2.0 to about 6.0 and preferably from about 3.5 to about 4.5. Preferred acids are selected from the group consisting of phosphoric acid, lactic acid, acetic acid, citric acid and mixtures thereof. Finally, the solution may be modified by the use of a gelling agent to permit more effective contact between the solution and the porcelain during the etching step. Preferred gelling agents are selected from the group consisting of xantham gum, carboxy methyl cellulose and hydroxypropyl cellulose.

DETAILED DESCRIPTION OF THE INVENTION

Because of its high toxicity, hydrogen fluoride is totally unacceptable as a material for etching porcelain. How every, buffered solutions containing trace amounts of hydrogen fluoride have, according to the principles of this invention, been found to be admirably suited for etching porcelain. Such solutions are normally formed by adding a salt, usually an alkali metal fluoride salt, to a dilute weak acid. For example, if several grams of sodium fluoride are dissolved in 100 grams of a weak acid, such as 0.1 molar $H_3PO_4$, there is a reasonable amount of hydrogen fluoride present at the pH of about 3.5 due to the equilibria presented in the following equations:

$$F^- + H^+ \rightleftharpoons HF$$

$$HF_2^- \rightleftharpoons HF + F^-$$

$$H_2F_3^- + H^+ + HF_2^- + F^- \rightleftharpoons HF + 2F^- + H^+$$

The use of such a solution maintains a constant but safe supply level of of hydrogen fluoride during the etching process, since as the hydrogen fluoride is consumed in reacting with the silicon dioxide contained in the porcelain, more hydrogen fluoride is produced due to the equilibria present in the buffered solution.

A number of experiments were performed to demonstrate the efficiencies of the present invention. Standard dental porcelain appliances and porcelain teeth were employed in all of the experiments. To determine whether or not adequate etching had taken place, attempts were made to bond Cervident ® restorative materials to the porcelain.

Any of the widely-used dental cements may be employed to bond various repair parts and the like to the etched porcelain. Among the dental cements are the zinc phosphate cements, silicates, zinc silicate cements, resin cements, which are primarily methyl methacrylate polymers having fillers added therein, zinc oxide-eugenol cements, poly carboxylate cements, which are mixtures of zinc oxide and aqueous solutions of polyacrylic acids, gypsum products, glass-ionomer cements, and the like. When composite materials are employed, a silane primer or adhesion is employed, followed by the application of the polymer composite restorative material, such as the Cervident® composite, which is a commercial product available worldwide.

A number of porcelain teeth were etched using various solutions according to the present invention and tested to determine the effectiveness of the etch, to thereby permit adhesion of materials to the porcelain. One particularly suitable solution is the FDA approved acidulated fluoro phosphate gel which is used in topical fluoride treatments. This gel contains approximately 2.3% sodium fluoride dissolved in 0.1 molar phosphoric acid and has a pH of about 3.5

On one set of porcelain teeth, a first sample was cleaned by alcohol drying, a silane primer was added followed by a Cervident® composite. After drying, it was found that there was essentially no adhesion of the composite to the porcelain tooth. In contrast, the above described fluoride gel was employed for approximately seven minutes, followed by water cleaning, air drying, alcohol drying, silane primer and the Cervident® composite. A very strong adhesion was noted. The resultant bonded composite on the porcelain tooth was then subjected to adhesion testing in a hot-cold cycling machine for 10,000 cycles. Even after 10,000 cycles, the bond showed excellent adhesion between the Cervident® composite and the porcelain.

A second solution was prepared using 4% by weight sodium fluoride dissolved in 0.1 molar $H_3PO_4$. The phosphoric acid was prepared by dissolving 11.2 grams of 85% concentrated phosphoric acid diluted to 1000 ml. Yet another fluoride gel was prepared using 2% by weight sodium fluoride in 0.2 molar phosphoric acid. After eight minutes of etching for both solutions, the solutions were removed. Adhesion tests of both of these pieces of etched porcelain was approximately as effective as the previously described results. No adhesion was found without the etching step. In another example, 0.1 molar lactic acid solution was used with approximately 2% by weight of sodium fluoride. Similarly, lactic acid at other concentrations and other acids such as acetic acid, citric acid and mixtures of the various acids may be employed to obtain the solutions of this invention.

Having thus described the invention, what is claimed is:

1. A method of repairing a porcelain dental device, in situ, comprising:
    cleaning the portion of porcelain to be repaired;
    contacting said porcelain with a buffered solution containing trace amounts of hydrogen fluoride for at least two minutes to etch said porcelain; and
    removing said solution and bonding a repair material to said etched portion of said porcelain.

2. The method of claim 1, wherein said pH is from about 3.5 to 4.5.

3. The method of claim 1, wherein said solution is maintained in contact with said porcelain for at least five minutes.

4. The method of claim 1, wherein said solution contains a quantity of alkali metal fluoride, dissolved in a dilute weak acid.

5. The method of claim 4, wherein said solution contains from about one to about three parts of sodium fluoride by weight dissolved in about 50 to 150 parts of dilute weak acid.

6. The method of claim 5, wherein said weak acid is from about 0.05 molar to about 0.5 molar.

7. The method of claim 5 wherein said acid has a buffered pH of from 2.0 to about 6.0.

8. The method of claim 5 wherein said acid has a buffered pH of from about 3.5 to about 4.5.

9. The method of claim 5 wherein said acid is selected from the group consisting of phosphoric acid, lactic acid, acetic acid, citric acid and mixtures thereof.

10. The method of claim 5 wherein said solution further contains a gelling agent.

11. The method of claim 10, wherein said gelling agent is selected from the group consisting of xantham gum, carboxy methyl cellulose and hydroxypropyl cellulose.

* * * * *